US011493751B2

(12) United States Patent
Tao et al.

(10) Patent No.: US 11,493,751 B2
(45) Date of Patent: Nov. 8, 2022

(54) SYSTEMS AND METHODS FOR COMPACT OPTICAL RELAY

(71) Applicant: Vanderbilt University, Nashville, TN (US)

(72) Inventors: Yuankai Tao, Nashville, TN (US); Joseph D. Malone, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 142 days.

(21) Appl. No.: 16/750,920

(22) Filed: Jan. 23, 2020

(65) Prior Publication Data

US 2020/0233207 A1 Jul. 23, 2020

Related U.S. Application Data

(60) Provisional application No. 62/795,918, filed on Jan. 23, 2019.

(51) Int. Cl.
*G02B 26/10* (2006.01)
*A61B 3/14* (2006.01)
*A61B 3/12* (2006.01)
*A61B 3/10* (2006.01)

(52) U.S. Cl.
CPC ............ *G02B 26/101* (2013.01); *A61B 3/102* (2013.01); *A61B 3/1225* (2013.01); *A61B 3/14* (2013.01)

(58) Field of Classification Search
CPC ...... G02B 26/101; G02B 13/22; A61B 3/102; A61B 3/1225; A61B 3/14
USPC ........................................................ 351/206
See application file for complete search history.

(56) References Cited

U.S. PATENT DOCUMENTS

| | | | |
|---|---|---|---|
| 5,298,939 A * | 3/1994 | Swanson | G03F 7/70275 355/30 |
| 5,867,305 A | 2/1999 | Waarts et al. | |
| 6,008,904 A | 12/1999 | Ishii et al. | |
| 6,211,988 B1 | 4/2001 | Engelhardt et al. | |
| 6,501,603 B2 | 12/2002 | Kasahara | |
| 7,400,804 B1 | 7/2008 | Di Teodoro et al. | |

(Continued)

OTHER PUBLICATIONS

Aguilar et al., "On the Limitations of the Confocal Scanning Optical Microscope as a Profilometer", Journal of Modern Optics: vol. 42, No. 9, pp. 1785-1794, 1995.

(Continued)

*Primary Examiner* — Mohammed A Hasan
(74) *Attorney, Agent, or Firm* — Michael Best & Friedrich LLP

(57) ABSTRACT

An optical relay comprises a first scan mirror configured to receive an input optical beam, and to reflect the input optical beam as a first intermediate optical beam; a telecentric mirror configured to receive the first intermediate optical beam, and to reflect the first intermediate optical beam as a second intermediate optical beam; a second scan mirror configured to receive the second intermediate optical beam, and to reflect the second intermediate optical beam as an output optical beam; and a lens system disposed between the telecentric mirror and the first and second scan mirrors, such that the first intermediate optical beam and the second intermediate optical beam pass through the lens system. The optical relay may be a component of an optical system which further includes an optical engine.

20 Claims, 11 Drawing Sheets

(56) References Cited

U.S. PATENT DOCUMENTS

| | | | |
|---|---|---|---|
| 7,436,585 | B1 | 10/2008 | Di Teodoro et al. |
| 7,605,926 | B1 | 10/2009 | Hetzler et al. |
| 7,751,118 | B1 | 7/2010 | Di Teodoro et al. |
| 8,848,199 | B2 | 9/2014 | Choi et al. |
| 9,207,408 | B1 | 12/2015 | Di Teodoro et al. |
| 9,564,730 | B2 | 2/2017 | Savage-Leuchs |
| 9,871,948 | B2 | 1/2018 | Papadopoulos et al. |
| 9,877,654 | B2 * | 1/2018 | Tesar ................. A61B 1/07 |
| 10,649,136 | B2 | 5/2020 | Weirich et al. |
| 2002/0126293 | A1 | 9/2002 | Deck |
| 2003/0011784 | A1 | 1/2003 | De Groot et al. |
| 2003/0160968 | A1 | 8/2003 | Deck |
| 2004/0005127 | A1 | 1/2004 | Kilner et al. |
| 2004/0052459 | A1 | 3/2004 | Battiato et al. |
| 2004/0065118 | A1 | 4/2004 | Kilner et al. |
| 2005/0128468 | A1 | 6/2005 | Murata |
| 2005/0225774 | A1 | 10/2005 | Freimann et al. |
| 2006/0221350 | A1 | 10/2006 | Murphy et al. |
| 2007/0024858 | A1 | 2/2007 | Takahashi |
| 2007/0126849 | A1 * | 6/2007 | Maeda ............. G02B 26/126 347/224 |
| 2008/0316500 | A1 | 12/2008 | Schulte et al. |
| 2011/0075976 | A1 | 3/2011 | Sutherland |
| 2011/0176191 | A1 * | 7/2011 | Matsuoka ............. G02B 13/22 359/197.1 |
| 2011/0249311 | A1 | 10/2011 | Engelhardt |
| 2012/0092461 | A1 * | 4/2012 | Fisker ............. G01B 11/2518 348/46 |
| 2012/0281223 | A1 | 11/2012 | Mortimer et al. |
| 2013/0010286 | A1 | 1/2013 | Zhao et al. |
| 2013/0331709 | A1 | 12/2013 | Le et al. |
| 2015/0015879 | A1 | 1/2015 | Papadopoulos et al. |
| 2015/0305618 | A1 * | 10/2015 | Buckland ........... G02B 21/0012 351/206 |
| 2016/0218477 | A1 | 7/2016 | Savage-Leuchs |
| 2017/0027437 | A1 * | 2/2017 | Neal ................. A61B 3/107 |
| 2018/0188447 | A1 | 7/2018 | Weirich et al. |
| 2019/0384006 | A1 | 12/2019 | Tao et al. |
| 2020/0341190 | A1 | 10/2020 | Weirich et al. |

OTHER PUBLICATIONS

Betzig et al., "Imaging Intracellular Fluorescent Proteins at Nanometer Resolution", Science 313, pp. 1642-1645, 2006.

Booth, "Adaptive optics in microscopy", Philos. Trans. R. Soc. Lond. Math. Phys. Eng. Sci. 365, 2829-2843, 2007.

Bourgenot et al., "3D adaptive optics in a light sheet microscope" Opt. Express 20, pp. 13252-13261, 2012.

Brouwer, "Matrix Methods in Optical Instrument Design" (1964).

Chen et al., "Lattice light-sheet microscopy: Imaging molecules to embryos at high spatiotemporal resolution" Science 346, 1257998, 2014.

Cheng et al., "Coherent Anti-Stokes Raman Scattering Microscopy: Instrumentation, Theory, and Applications", J. Phys. Chem. B 108, p. 827-840, 2004.

Chlebus et al., "Direct measurement of group dispersion of optical components using white-light spectral interferometry", Opto Electron. Rev. 15, pp. 144-148, 2007.

Choi et al., "Phase sensitive swept-source optical coherence tomography imaging of the human retina with a vertical cavity surface-emitting laser light source", Optical Letters, vol. 38, No. 3, Feb. 2013, pp. 338-340.

Denk et al., "Two-photon laser scanning fluorescence microscopy" Science 248, pp. 73-76, 1990.

Dhalla et al., "Complex conjugate resolved heterodyne swept source opitcal coherence tomography using coherence revival", Biomedical Optics Express, vol. 3, No. 3, Feb. 2012, 17 pages.

Diddams et al., "Dispersion measurements with white-light interferometry" JOSA B 13, pp. 1120-1129, 1996.

Dufour et al., "Low-coherence interferometry—An advanced technique for optical metrology in industry" Insight—Non Destructive Testing and Condition Monitoring, Apr. 2005, 8 pages.

Francis et al., "Spectrometer-based refractive index and dispersion measurement using low-coherence interferometry with confocal scanning" Opt. Express 26, pp. 3604-3617, 2018.

Freund et al., "Connective tissue polarity. Optical second-harmonic microscopy, crossed-beam summation, and small-angle scattering in rat-tail tendon", Biophys. J. 50, pp. 693-712, 1986.

Fukano et al., "Separation of measurement of the refractive index and the geometrical thickness by use of a wavelength-scanning interferometer with a confocal microscope", Appl. Opt. 38, pp. 4065-4073, 1999.

Fukano et al., "Simultaneous measurement of thicknesses and refractive indices of multiple layers by a low-coherence confocal interference microscope", Opt. Lett. 21, pp. 1942-1944, 1996.

Galli et al., "Direct measurement of refractive-index dispersion of transparent media by white-light interferometry", Appl. Opt. 42, pp. 3910-3914, 2003.

Gerrard et al., "Introduction to Matrix Methods in Optics" (Courier Corporation, 1994).

Gustafsson, "Surpassing the lateral resolution limit by a factor of two using structured illumination microscopy", J. Microsc. 198, pp. 82-87, 2000.

Haruna et al., "Simultaneous measurement of the phase and group indices and the thickness of transparent plates by low-coherence interferometry" Opt. Lett. 23, pp. 966-968, 1998.

Hein et al., "Stimulated emission depletion (STED) nanoscopy of a fluorescent protein-labeled organelle inside a living cell", Proc. Natl. Acad. Sci. 105, p. 14271-14276, 2008.

Hell et al., "Breaking the diffraction resolution limit by stimulated emission: stimulated-emission-depletion fluorescence microscopy", Opt. Lett. 19, pp. 780-782, 1994.

Huang et al., "Optical coherence tomography", Science, vol. 254, Nov. 1991, pp. pp. 1178-1181.

Huisken et al. "Optical Sectioning Deep Inside Live Embryos by Selective Plane Illumination Microscopy" Science 305, pp. 1007-1009, 2004.

International Search Report and Written Opinion for related Application No. PCT/US2018/015531 dated May 25, 2018 (11 pages).

International Search Report and Written Opinion for related Application No. PCT/US2019/015148 dated May 24, 2019 (17 pages).

Ji et al., "Characterization and adaptive optical correction of aberrations during in vivo imaging in the mouse cortex", Proc. Natl. Acad. Sci. 109, pp. 22-27, 2012.

Kumar et al., "Using interference in the frequency domain for precise determination of thickness and refractive indices of normal dispersive materials", JOSA B 12, pp. 1559-1563, 1995.

Kurvits et al., "Comparative analysis of imaging configurations and objectives for Fourier microscopy" J. Opt. Soc. Am. A 32, 2082, 2015.

Lin et al., "6×6 matrix formalism of optical elements for modeling and analyzing 3D optical systems", Appl. Phys. B 97, pp. 135-143, 2009.

Liu et al., "All-fiber, high power single-frequency linearly polarized ytterbium-doped fiber amplifier" Chinese Optics Letters, vol. 9, No. 3., Mar. 10, 2011; figure 1; p. 031402-1, paragraph 5-p. 031402-1, paragraph 3.

Malacara-Doblado, D. & Ghozeil, I. Hartmann, Hartmann-Shack, and Other Screen Tests, in Optical Shop Testing (ed. Daniellacara) pp. 361-397, 2007.

Martinez-Enriquez et al., "OCT-based full crystalline lens shape change during accommodation in vivo", Biomed. Opt. Express 8, pp. 918-933, 2017.

Maruyama et al., "Low-coherence interferometer system for the simultaneous measurement of refractive index and thickness" Appl. Opt. 41, pp. 1315-1322, 2002.

Na et al., "Self-referenced spectral interferometry for simultaneous measurements of thickness and refractive index", Appl. Opt. 48, pp. 2461-2467, 2009.

Olivier et al., "Dynamic aberration correction for multiharmonic microscopy" Opt. Lett. 34, pp. 3145-3147, 2009.

Ortiz et al. "Optical coherence tomography for quantitative surface topography" Appl. Opt. 48, pp. 6708-6715 (2009).

(56) References Cited

OTHER PUBLICATIONS

Ortiz et al., "Optical distortion correction in Optical Coherence Tomography for quantitative ocular anterior segment by three-dimensional imaging" Opt. Express 18, pp. 2782-2796 (2010).

Ortiz et al., "Optical distortion correction in Optical Coherence Tomography for quantitative ocular anterior segment by three-dimensional imaging," Opt. Express 18, 2782-2796 (2010).

Piratelli-Filho et al., "Error evaluation in reverse engineering of aspherical lenses" 17th International Congress of Metrology, 13007, EDP Sciences, 2015.

Poddar et al., "In vivo imaging of human vasculature in the chorioretinal complex using phase-variance contrast method with phase-stabilized 1-um swept-source optical coherence tomography", Journal of Biomedical Optics, vol. 19., No. 12, Dec. 2014, pp. 126010-1-126010-12.

Royer et al., "A practical guide to adaptive light-sheet microscopy", Nat. Protoc. 13, 2462 (2018).

Rust et al., "Sub-diffraction-limit imaging by stochastic optical reconstruction microscopy (STORM)", Nat. Methods 3, pp. 793-796, 2006.

Sáinz et al., "Real time interferometric measurements of dispersion curves" Opt. Commun. 111, pp. 632-641, 1994.

Silvestri et al., "Correcting spherical aberrations in confocal light sheet microscopy: A theoretical study", Microsc. Res. Tech. 77, pp. 483-491 (2014).

Sinefeld et al., "Adaptive optics in multiphoton microscopy: comparison of two, three and four photon fluorescence" Opt. Express 23, pp. 31472-31483, 2015.

Stirman et al., "Wide field-of-view, multi-region, two-photon imaging of neuronal activity in the mammalian brain" Nat. Biotechnol. 34, pp. 857-862, 2016.

Tearney et al., "Determination of the refractive index of highly scattering human tissue by optical coherence tomography", Opt. Lett. 20, pp. 2258-2260, 1995.

Tomlins et al., "Simultaneous analysis of refractive index and physical thickness by Fourier domain optical coherence tomography" IEE Proc.—Optoelectron. 153, pp. 222-228, 2006.

Uhlhorn et al., "Refractive Index Measurement of the Isolated Crystalline Lens Using Optical Coherence Tomography," Vision Res. 48, pp. 2732-2738, 2008.

Wang et al., "Depth-encoded all-fiber swept source polarization sensitive OCT", Biomedical Optics Express, vol. 5, No. 9, Aug. 2014, 19 pages.

Wojtkowski et al., "Ultrahigh-resolution, high-speed, Fourier domain optical coherence tomography and methods for dispersion compensation" Opt. Express 12, pp. 2404-2422, 2004.

Wu et al., "Faster, sharper, and deeper: structured illumination microscopy for biological imaging", Nat. Methods 1, 2018.

Xu et al., "Multiphoton fluorescence excitation: new spectral windows for biological nonlinear microscopy", Proc. Natl. Acad. Sci. 93, pp. 10763-10768, 1996.

Youngquist et al., "Optical coherence-domain reflectometry: a new optical evaluation technique" Opt. Lett. 12, pp. 158-160, 1987.

Zinter et al., "Maximizing fluorescence collection efficiency in multiphoton microscopy" Opt. Express 19, pp. 15348-15362, 2011.

Zipfel et al., "Nonlinear magic: multiphoton microscopy in the biosciences" Nat. Biotechnol. 21, pp. 1369-1377, 2003.

Abrams et al., "Speed and accuracy of saccadic eye movements: characteristics of impulse variability in the oculomotor system", J. Exp Psychol Hum Percept Perform, vol. 15, No. 3, 1989, pp. 529-543.

Braaf et al., "Real-time eye motion correction in phase resolved OCT angiography with tracking SLO", Biomedical Optics Express, vol. 4, No. 1, 2012, pp. 51-65.

Cabrera et al., "Exudative retinal detachment documented by handheld spectral domain optical coherence tomography after retinal laser photocoagulation for retinopathy of prematurity", Retina Cases Brief Res, 1, 2018.

Campbell et al., "Handheld optical coherence tomography angiography and ultra-wide-field optical coherence tomography in retinopathy of prematurity", JAMA Ophthalmology, vol. 135, No. 9, 2017, pp. 977-981.

Chavala et al., "Insights into advanced retinopathy of prematurity using handheld spectral domain optical coherence tomography imaging", Ophthalmology, vol. 116, No. 12, 2009, pp. 2448-2456.

Chen et al., "Eye-motion-corrected optical coherence tomography angiography using Lissajous scanning", Biomedical Optics Express, vol. 9, No. 3, 2018, pp. 1111-1129.

Chen et al., "Three-dimensional eye motion correction by Lissajous scan optical coherence tomography", Biomedical Optics Express, vol. 8, No. 3, 2017, pp. 1783-1802.

Choi et al., "Ultrahigh-speed, swept-source optical coherence tomography angiography in nonexudative age-related macular degeneration with geography atrophy", Ophthalmology, vol. 122, No. 12, 2015, pp. 2532-2544.

Choma et al., "Sensitivity advantage of swept source and Fourier doman opitcal coherence tomography", Optics Express, vol. 11, No. 18, 2003, pp. 2183-2189.

Demene et al., "Spatiotemporal clutter filtering of ultrafast ultrasound date highly increases Doppler and ultrasound sensitivity", IEEE Transactoins on Medical Imaging, vol. 34, No. 11, 2015, pp. 2271-2285.

DuBose et al., "Handheld adaptive optics scanning laser ophthalmoscope", Optica, vol. 5, No. 9, 2018, pp. 1027-1036.

Elble, "Central Mechanisms of tremor", J. Clin. Neurophysiol, vol. 13, No. 2, 1996, pp. 133-144.

El-Haddad et al., "Spectrally encoded coherence tomography and reflectometry: simultaneous en face and cross-sectional imaging at 2 gigapixels per second", J. Biophotonics, vol. 11, No. 4, 2018, p. e201700268.

Frangi et al., "Multiscale Vessel Enhancement Filtering", Springer, 1998, pp. 130-137.

Gerth et al., "High-resolution retinal imaging in young children using a handheld scanner and Fourier-domain optical coherence tomogrpahy", J. Am. Assoc. Pediatrics Ophthalmology Strabismus, vol. 13, No. 1, 2009, pp. 72-74.

Guizar-Sicairos et al., "Efficient subpixel image registration algorithms", Opt Lett, vol. 33, No. 2, 2008, pp. 156-158.

Helb et al., "Clinical evaluation of simultaneous confocal scanning laser ophthalmoscopy imaging combined with high-resolution, spectral-domain optical coherence tomogrpahy", Acta Ophthalmology, vol. 88, No. 8, 2010, pp. 842-849.

Huber et al., "Fourier domain mode locking at 1050 nm for ultra-high-speed optical coherence tomography of the human retina at 236,000 axial scans per second", Opt. letter, vol. 32, No. 14, 2007, pp. 2049-2051.

Huo et al., "Ultrahigh-speed optical coherence tomography utilizing all-optical 40 MHz swept-source", J Biomed Opt, vol. 20, No. 3, 2015, p. 030503.

Joshi et al., "Optical coherence tomography findings in stage 4A retinopathy of prematurity", Ophthalmology, vol. 113, No. 4, 2006, pp. 657-660.

Jung et al., "Handheld optical coherence tomography scanner for primary care diagnostics", IEEE Transactions on Biomedical Engineering, vol. 58, No. 3, 2011, pp. 741-744.

Klein et al., "High-speed OCT light sources and systems [Invited]", Biomedical Optics Express, vol. 8, No. 2, 2017, pp. 828-859.

Kraus et al., "Motion correction in opitcal coherence tomography volumes on a per A-scan basis using orthogonal scan patterns", Biomedical Optics Express, vol. 3, No. 6, 2012, pp. 1182-1199.

LaRocca et al., "Handheld simultaneous scanning laser ophthalmoscopy and optical coherence tomography system", Biomedical Optics Express, vol. 4, No. 11, 2013, pp. 2307-2312.

Laurutis et al., "The vestibulo-ocular reflex during human saccadic eye movements", J. Physiol., vol. 373, 1986, pp. 209-233.

Le et al., "Robust principal component analysis in optical microangiography", Quant Imaging Med Surg, vol. 7, No. 6, 2017, pp. 654-667.

(56) References Cited

OTHER PUBLICATIONS

Lee et al., "Macular features from spectral-domain optical coherence tomography as an adjunct to indirect ophthalmoscopy in retinopathy of prematurity", Retina, vol. 31, No. 8, 2011, pp. 1470-1482.
Lu et al., "Handheld ultrahigh speed swept source optical coherence tomography instrument using a MEMS scanning mirror", Biomedical Optics Express, vol. 5, No. 1, 2014, pp. 293-311.
Mallipatna et al., "The use of handheld spectral domain optical coherence tomography in pediatric ophthalmology practice: our experience of 975 infants and children", Indian J. Ophthalmol, vol. 63, No. 7, 2015, pp. 586-593.
Malone et al., "Simultaneous multimodal ophthalmic imaging using swept-source spectrlaly encoded scanning laser ophthalmoscopy and optical coherence tomography", Biomedical Optics Express, vol. 8, No. 1, 2017, pp. 193-206.
Martinez-Conde et al., "The role of fixational eye movements in visual perception", Nat. Rev Neuroscie, vol. 5, No. 3, 2004, pp. 229-240.
Moult et al., "Ultrahigh-speed swept-source OCT angiography in exudative AMD", Ophthalmic Surgery Lasers Imaging Retina, vol. 45, No. 6, 2014, pp. 496-505.
Nankivil et al., "Handheld, rapidly switchable, anterior/posterior segment swept source opitcla coherence tomography probe", Biomedical Optics Express, vol. 6, No. 11, 2015, pp. 4516-4528.
Ng et al., "Fundus fluorescein angiography in the screening for and management of retinopathy of prematurity", J Pediatr. Ophthalmol Strabismus, vol. 43, No. 2, 2006, pp. 85-90.
Patel, "Optical coherence tomography in the management of acute retinopathy of prematurity", Am J. Ophthalmol, vol. 141, No. 3, 2006, pp. 582-584.
Pircher et al., "Simultaneous SLO/OCT imaging of the human retina with axial eye motion correction", Optics Express, vol. 15, No. 25, 2007, pp. 16922-16923.
Polans et al., "Asymmetric wide-field optical model of the human eye with tilted and decentered crystalline lens that reproduces experimentally measured abberations: errata", Optica, vol. 5, No. 11, 2018, pp. 1461.
Polans et al., "Wide-field optical model of the human eye with asymmetrically tilted and decentered lens that reproduces measured ocular aberrations", Optica, vol. 2, No. 2, 2015, pp. 124-134.
Satue et al., "Use of Fourier-domain OCT to detect retinal nerve fiber layer degeneration in Parkinson's disease patients", Eye, vol. 27, No. 4, 2013, pp. 507-514.
Sheehy et al., "High-speed, image-based eye tracking with a scanning laser ophthalmoscope", Biomedical Optics Express, vol. 3, No. 10, 2012, pp. 2611-2622.
Song et al., "Development of a clinical prototype of a miniature hand-held optical coherence tomography probe for prematurity and pediatric ophthalmic imaging", Biomedical Optics Express, vol. 10, No. 5, 2019, pp. 2383-2398.
Tao et al, "Interlaced spectrally encoded confocal scanning laser ophthalmoscopy and spectral domain optical coherence tomography", Biomedical Optics Express, vol. 1, No. 2, 2010, pp. 431-440.
Tong et al., "Evaluation of optic nerve development in preterm and term infants using handheld spectral-domain optical coherence tomography", Ophthalmology, vol. 121, No. 9, 2014, pp. 1818-1826.
Viehland et al., "Ergonomic handheld OCT angiography probe optimized for pediatric and supine imaging", Biomedical Optics Express, vol. 10, No. 5, 2019, pp. 2623-2638.
Vinekar et al., "Understanding clinically undetected macular changes in early retinopathy of prematurity on spectral domain optical coherence tomography", Invest Opthalmol Vis Sci, vol. 52, No. 8, 2011, pp. 5183-8188.
Zang et al., "Automated motion correcting using parallel-strip registration for wide-field en face OCT angiogram", Biomedical Optics Express, vol. 7, No. 7, 2016, pp. 2823-2836.
Zhang et al., "In vivo wide-field multispectral scanning laser ophthalmoscopy-optical coherence tomography mouse retinal imager: longitudinal imaging of ganglion cells, microglia, and Muller glia, and mapping of the mouse retinal and choroidal vasculature", Journal of Biomed Opt, vol. 20, No. 12, 2015, pp. 126005.
Zhang et al., "Methods and algorithms for optical coherence tomography-based angiography: a review and comparison", J. Biomed Opt, vol. 20, No. 10, 2015, pp. 100901.

\* cited by examiner

SYSTEMS AND METHODS FOR COMPACT OPTICAL RELAY

CROSS-REFERENCE TO RELATED APPLICATIONS

This application claims priority to U.S. Provisional Application No. 62/795,918, filed on Jan. 23, 2019, the entire contents of which are herein incorporated by reference.

BACKGROUND

1. Field of the Disclosure

This application relates generally to optical systems. More specifically, this application relates to systems and methods incorporating imaging relays in various optical applications.

2. Description of Related Art

Four-focal-length ("4-f") imaging relays may be used in different optical systems to magnify or de-magnify the spot size of a beam. This may be applicable in scanning systems, where multiple scanning mirrors are to be imaged onto conjugate pupil planes to achieve telecentricity. The amount of magnification provided by a system is directly proportional to the ratio of the focal lengths of the two lens components. Thus, the length of the system is determined by the focal lengths of each lens; that is, the amount of magnification desired results in a lower bound on the size of the relay. In optical designs, the length and complexity of the overall system is often limited by 4-f imaging relays.

FIG. 1A illustrates an exemplary 4-f imaging relay 100a. The 4-f imaging relay 100a includes a first lens 101 having a first focal length $f_1$ and a second lens 102 having a second focal length $f_2$. For purposes of illustration, the first lens 101 and the second lens 102 are illustrated as doublets. The distance between the first lens 101 and the second lens 102 is $f_1+f_2$.

In order to minimize the length of an optical system, a single lens imaging relay may replace the 4-f imaging relay. FIG. 1B illustrates an exemplary single lens imaging relay 100b. The single lens imaging relay 100b includes a single lens 103 having a focal length f. Due to its single lens nature, the single lens relay 100b eliminates the intermediate Fourier plane (or infinity space for non-scanning applications). Many microscopy techniques utilize the intermediate Fourier plane to introduce other optical elements, such as filters, phase-shifters, apertures, and the like, or to fold in another optical path to combine multiple imaging modalities. Thus, such applications require access to the intermediate Fourier plane.

One such application is quantitative ophthalmic imaging. Ophthalmic imaging may be implemented using optical coherence tomography ("OCT"), which enables volumetric visualization of subsurface tissue microstructures. Existing OCT systems utilize a benchtop design that requires patients to be imaged in a seated upright position. However, visualization of peripheral retinal structures may be difficult due to the limited mechanical range of motion of the OCT scan head for such systems. Moreover, long acquisition protocols such as those used for OCT angiography ("OCTA") make OCT/OCTA imaging in uncooperative, bedridden, or pediatric patients difficult or impractical.

OCT may suffer from motion artifacts, which are dominated by microsaccades (approximately 15 to 150 deg/s) and ocular drift (approximately 0.5 deg/s). In handheld imaging, these artifacts may further be compounded by photographer motion and tremor (approximately 8 to 12 Hz). These artifacts may affect the anatomic accuracy of OCT volumetric data and can lead to errors in quantitative image analysis.

Accordingly, there exists a need for compact imaging relays which allow access to the intermediate Fourier plane. Furthermore, there exists a need for an OCT probe incorporating such relays which does not suffer from the above difficulties.

BRIEF SUMMARY OF THE DISCLOSURE

Various aspects of the present disclosure relate to optical systems and methods which minimize the overall length and complexity of the optical relay and which maintain the intermediate Fourier plane.

In one exemplary aspect of the present disclosure, there is provided an optical relay comprising a first scan mirror configured to receive an input optical beam, and to reflect the input optical beam as a first intermediate optical beam; a telecentric mirror configured to receive the first intermediate optical beam, and to reflect the first intermediate optical beam as a second intermediate optical beam; a second scan mirror configured to receive the second intermediate optical beam, and to reflect the second intermediate optical beam as an output optical beam; and a lens system disposed between the telecentric mirror and the first and second scan mirrors, such that the first intermediate optical beam and the second intermediate optical beam pass through the lens system.

In another exemplary aspect of the present disclosure, there is provided an optical system comprising: an optical engine including a light source configured to emit a source light, and at least one optical fiber configured to transmit the source light to an output of the optical engine; and a probe including an optical relay, the optical relay including a first scan mirror configured to receive an input optical beam, and to reflect the input optical beam as a first intermediate optical beam; a telecentric mirror configured to receive the first intermediate optical beam, and to reflect the first intermediate optical beam as a second intermediate optical beam; a second scan mirror configured to receive the second intermediate optical beam, and to reflect the second intermediate optical beam as an output optical beam; and a lens system disposed between the telecentric mirror and the first and second scan mirrors, such that the first intermediate optical beam and the second intermediate optical beam pass through the lens system In this manner, various aspects of the present disclosure provide for improvements in at least the technical fields of microscopy, ophthalmology, imaging, and image processing.

This disclosure can be embodied in various forms, including optical systems operated by hardware or circuits controlled by computer-implemented methods, computer program products, computer systems and networks, user interfaces, and application programming interfaces; as well as hardware-implemented methods, signal processing circuits, memory arrays, application specific integrated circuits, field programmable gate arrays, and the like. The foregoing summary is intended solely to give a general idea of various aspects of the present disclosure, and does not limit the scope of the disclosure in any way.

DESCRIPTION OF THE DRAWINGS

The patent or application file contains at least one drawing executed in color. Copies of this patent or patent application publication with color drawing(s) will be provided by the Office upon request and payment of the necessary fee.

These and other more detailed and specific features of various embodiments are more fully disclosed in the following description, reference being had to the accompanying drawings, in which.

DETAILED DESCRIPTION

In the following description, numerous details are set forth, such as optical system configurations, imaging devices and operations, circuit operations, and the like, in order to provide an understanding of one or more aspects of the present disclosure. It will be readily apparent to one skilled in the art that these specific details are merely exemplary and not intended to limit the scope of this application.

Moreover, while the present disclosure focuses mainly on examples in which the various circuits are used in microscopy and, more specifically, optical coherence tomography, it will be understood that this is merely one example of an implementation. It will further be understood that the disclosed systems and methods can be used in any optical device in which there is a need to minimize size while maintaining access to the intermediate Fourier plane; for example, confocal and fluorescence imaging, scanning laser ophthalmoscopy, non-microscopy imaging, optical communications, and so on.

Exemplary Imaging Systems

Figure 1A:
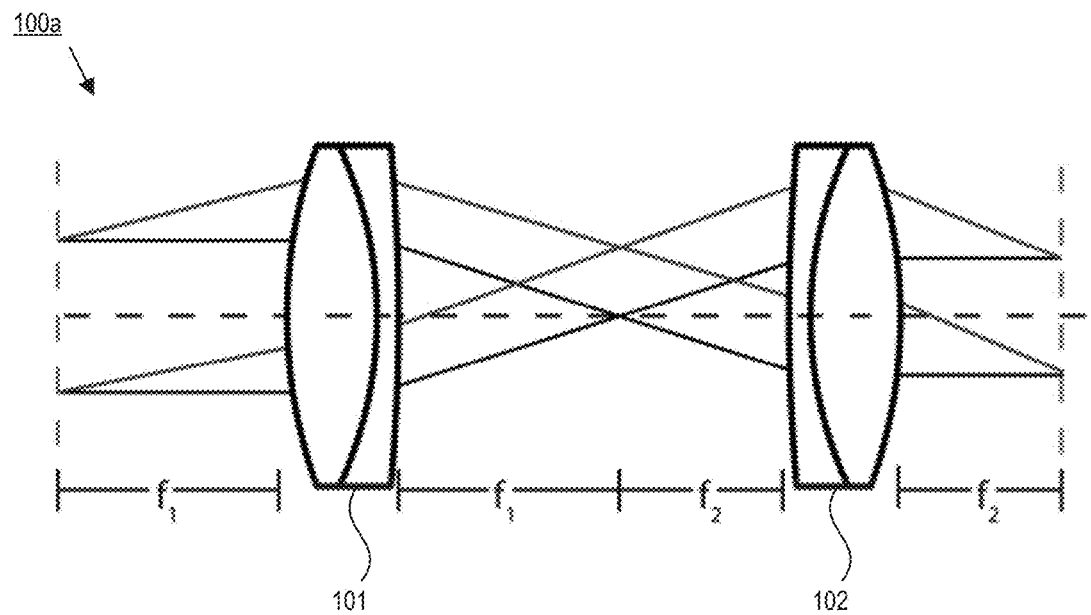
FIGS. 1A-B illustrate comparative example imaging relays.
Figure 1B:
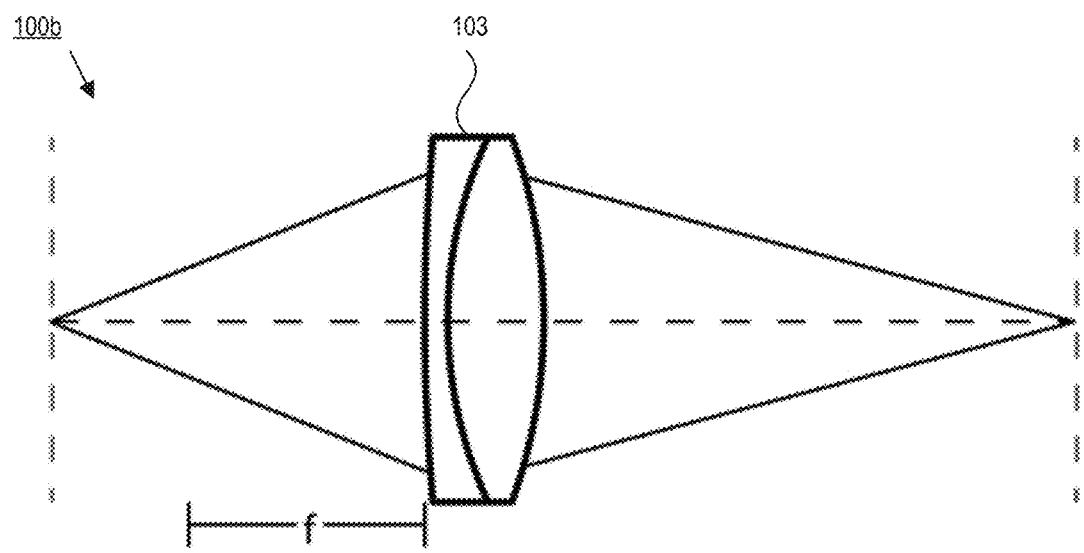
Figure 2:
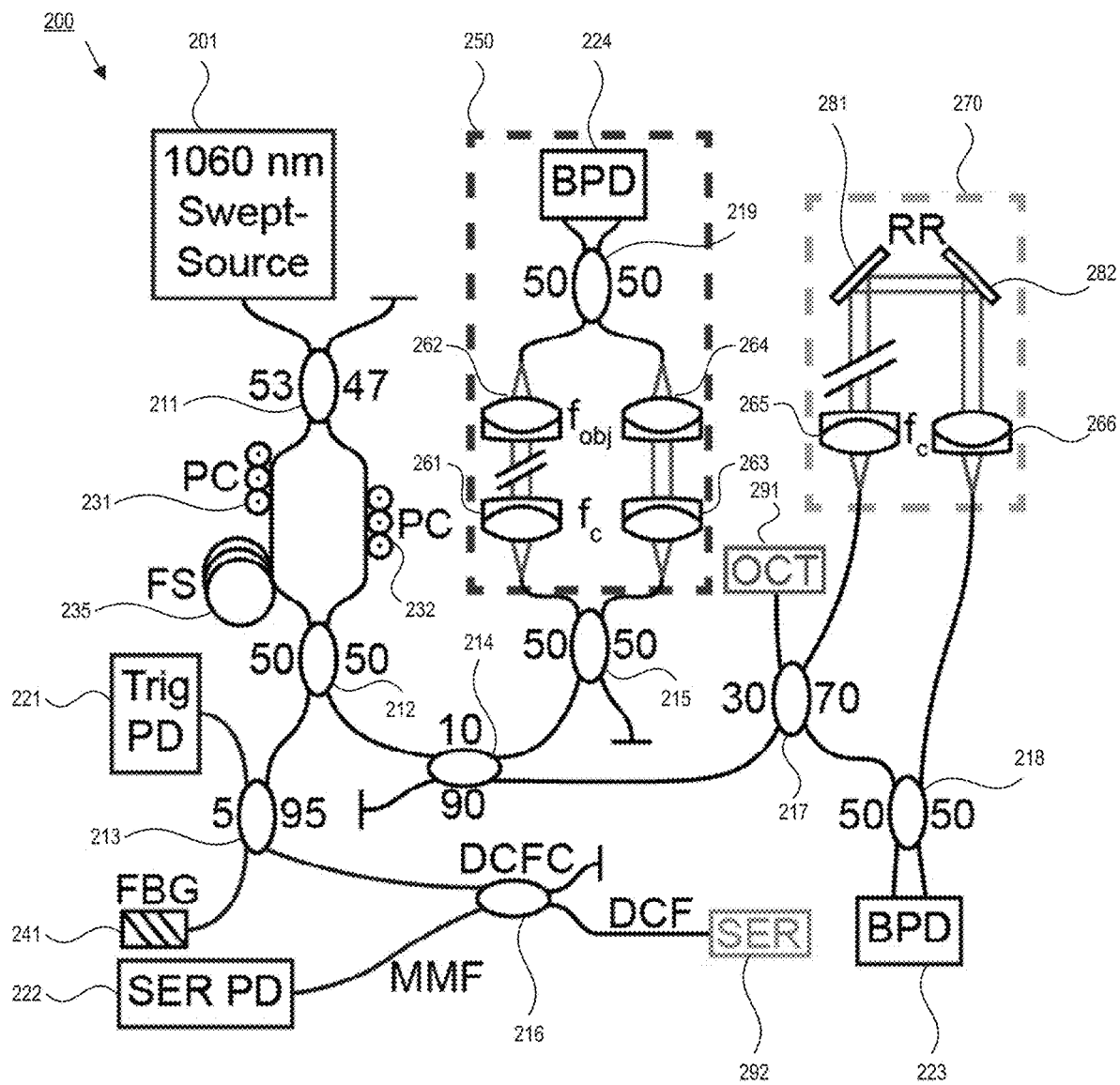
FIG. 2 illustrates an exemplary optical engine in accordance with various aspects of the present disclosure.
Figure 3A:
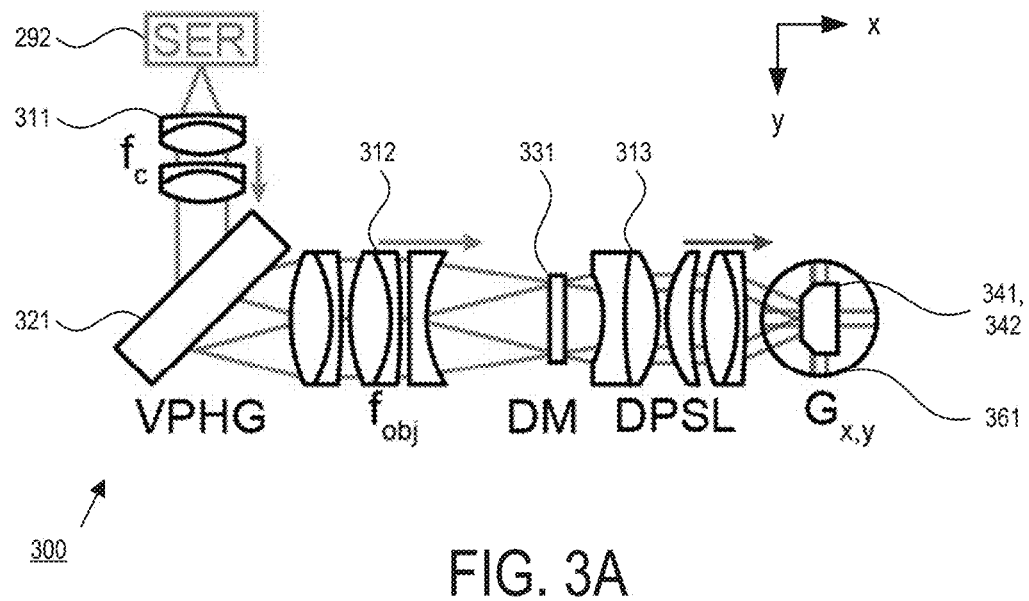
FIGS. 3A-B illustrate an exemplary optical probe in accordance with various aspects of the present disclosure.
Figure 3B:
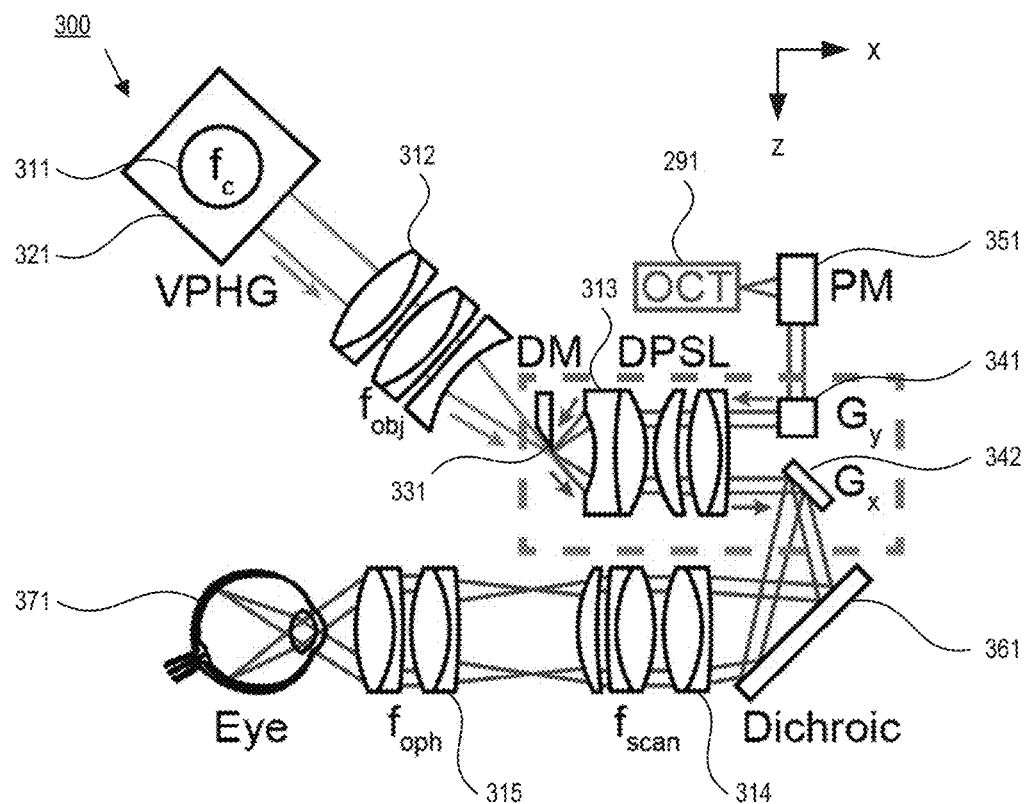

The present disclosure may be applied to several applications, including quantitative ophthalmic imaging. FIGS. 2 and 3A-B illustrate one such application, in which an imaging system is provided which implements spectrally encoded coherence tomography and reflectometry ("SECTR"). SECTR integrates OCT with spectrally encoded reflectance ("SER") imaging. SER uses line-scan illumination by spectrally dispersing a broadband light source and encoding spatial position as a function of wavelength. The SER and OCT optical paths are coaligned and signals may be simultaneously sampled using a high-speed digitizer for reduced system complexity and simultaneous acquisition of en face SER frames with each OCT cross section at greater than 200 frames per second ("fps"). SECTR utilizes a shared galvanometer scanner (or other scan mirror) to ensure inherent spatiotemporal coregistration between OCT and SER data. In one example, the imaging system includes a SECTR engine 200 as illustrated in FIG. 2 and a handheld probe 300 as illustrated in FIGS. 3A-B.

As illustrated in FIG. 2, the SECTR engine 200 includes a light source 201, a plurality of beam couplers 211-219, a plurality of sensors 221-224, a pair of polarization converters 231-232, a fiber 235, a fiber Bragg grating 241, a k-clock device 250, a plurality of lens systems 261-266, a reference arm 270, a pair of reflective elements 281-282, an OCT sample fiber 291, and a SER sample fiber 292. In the illustration, the numbers on each side of the plurality of beam couplers 211-219 indicate the mixing and/or splitting percentages. FIG. 2 illustrates, as an example of the light source 201, a 200 kHz 1060-nm center wavelength swept-source laser with optical buffering to 400 kHz. Each of the lens systems 261-266 are illustrated as doublets. The various elements of FIG. 2 may be optically connected by a plurality of optical fibers, which may be of a multimode fiber ("MMF") type, a double-clad fiber ("DCF") type, and the like. The beam coupler 216, in particular, is illustrated as a double-clad fiber coupler ("DCFC") and will be described in more detail below. Furthermore, FIG. 2 illustrates, as examples of sensors 221-224, a plurality of photodiodes. Some of the photodiodes may be implemented as a balanced photodetector ("BPD"). In some implementations, other light source technologies, transmission optics technologies, and/or sensing technologies may be utilized.

Moreover, while FIG. 2 illustrates several particular optical elements, it should be understood that this illustration is merely exemplary and that other implementations may be used; for example, implementations which include more and/or fewer of particular optical components so long as the SER and OCT optical paths are coaligned.

The OCT sample fiber 291 and the SER sample fiber 292 are coupled to corresponding inputs in the handheld probe 300, as illustrated in FIGS. 3A-B. In particular, FIG. 3A illustrates a planar view (specifically, from a perspective in the −z direction) of the handheld probe 300, whereas FIG. 3B illustrates a side view (specifically, from a perspective in the +y direction) of the handheld probe 300. In addition to input couplings for the OCT sample fiber 291 and the SER sample fiber 292, the handheld probe includes collimating optics 311, focusing optics 312, double-pass optics 313, scan optics 314, and ophthalmic optics 315; a volume-phase holographic grating 321; a d-shaped pickoff mirror 331; a pair of galvanometers 341-342; a parabolic mirror 351; a dichroic mirror 361; and a target 371 (illustrated as a human eye). The double-pass optics 313, the d-shaped pickoff mirror 331, and the galvanometers 341-342 collectively constitute a double-pass scan lens ("DPSL") system, which will be described in more detail below. Arrows along the optical path in FIGS. 3A-B illustrate the direction of light propagation in the handheld probe 300.

Double-Pass Scan Lens

The DPSL is an example of an optical relay in accordance with the present disclosure. Among other aspects, the DPSL provides a comparatively compact form factor and allows access to the intermediate Fourier plane. The galvanometers 341-342 are examples of first and second scan mirrors in accordance with the present disclosure; in some implementations, the scan mirrors may be other types of reflective elements. The d-shaped pickoff mirror 331 is an example of a telecentric mirror in accordance with the present disclosure. The double-pass optics 313 are an example of a lens system in accordance with the present disclosure. The lens system itself may be composed of multiple individual optical elements (e.g., individual lenses). As can be seen in FIGS. 3A-B and will be discussed in more detail below, the first galvanometer 341 is configured to receive an input optical beam and to reflect the input optical beam as a first intermediate optical beam. The d-shaped pickoff mirror 331 is to receive the first intermediate optical beam and to reflect the first intermediate optical beam as a second intermediate optical beam. The second galvanometer 342 is configured to receive the second intermediate optical beam and to reflect the second intermediate optical beam as an output optical beam.

The lens system is disposed between the telecentric mirror and the first and second galvanometers, such that both the first intermediate optical beam and the second intermediate optical beam pass through the lens system. In one example, the telecentric mirror is separated from the lens system by a distance equal to the focal length of the lens system in the −x direction (shown in FIGS. 3A-B) and the first and second scan mirrors are separated from the lens system by a distance equal to the focal length of the lens system in the +x direction (shown in FIGS. 3A-B). As such, the first and second scan mirrors, the lens system, and the telecentric mirror are arrayed in a folded 4-f relay configuration. Moreover, the first and second scan mirrors are displaced from one another in the y direction. Because of this lateral displacement, the first intermediate optical beam and the second intermediate optical beam pass through different regions of the lens system. This results in improved relay performance by, for example, balancing out aberrations.

In one particular example, the DPSL includes physical parameters as detailed in Table 1 below. These values are exemplary and may be subject to modification without departing from the scope of the present disclosure. For example, while Table 1 lists <50.8 mm and <200 mm as preferred values for the lens diameter and length of system, respectively, some implementations of the present disclosure may utilize <44.1 mm and <184 mm as preferred values for the lens diameter and length of system, respectively.

TABLE 1

| Parameter | Value |
| --- | --- |
| Entrance Pupil Diameter | 10 mm |
| FOV | ±15° |
| Wavelength | 1000-1100 nm |
| Magnification | 1 |
| RMS Wavefront | <0.05 |
| Distortion | <1% |
| Maximum Ray Angle of Incidence and Refraction on Surfaces | <45° |
| Maximum Chief Ray Angle on Mirror | <.1° |
| Lens Diameter | <50.8 mm |
| Lens System Focal Length | 68-80 mm |
| System Length | <200 mm |
| Distance from Nearest Lens Surface to Mirror | >5 mm |
| Distance from Galvanometers to Nearest Lens Surface | >5 mm |
| Number of Lens Elements | ≤5 |

Figure 4A:
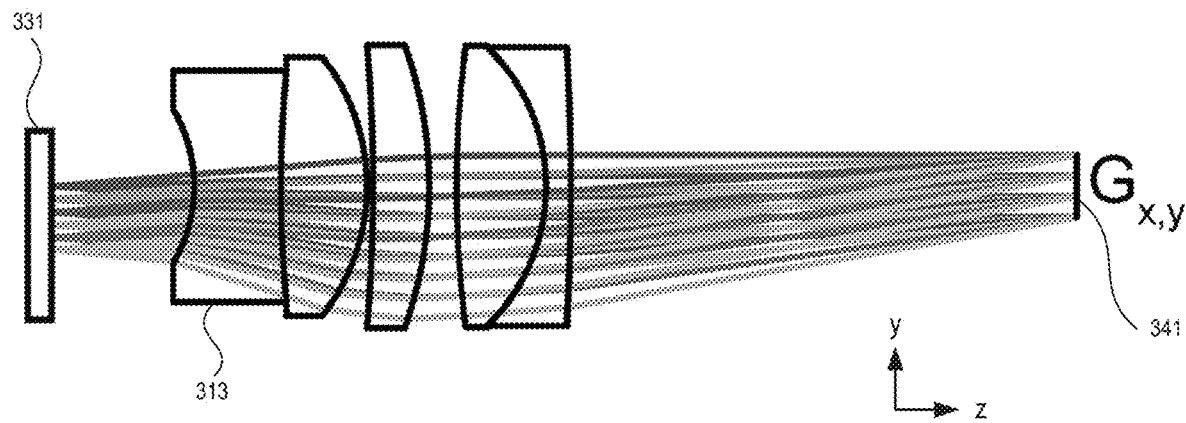
FIGS. 4A-C illustrate an exemplary optical relay in accordance with various aspects of the present disclosure.
Figure 4B:
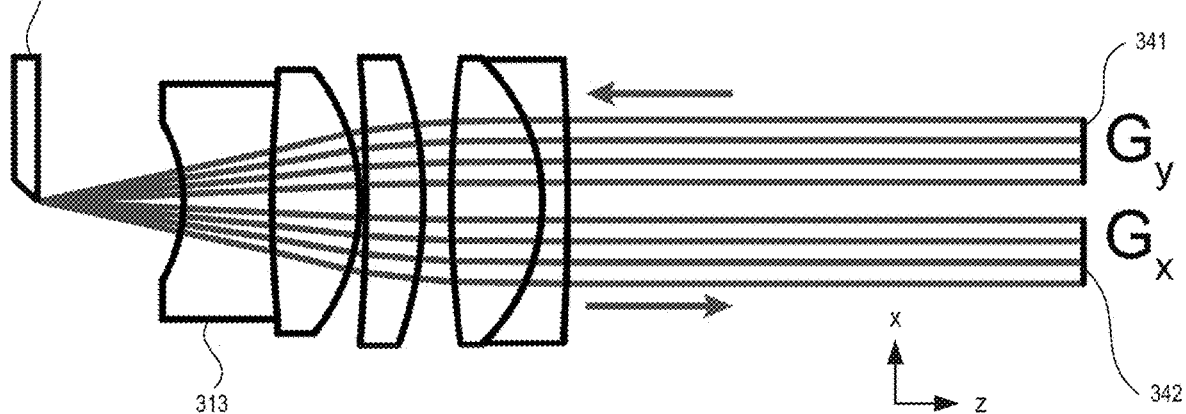
Figure 4C:
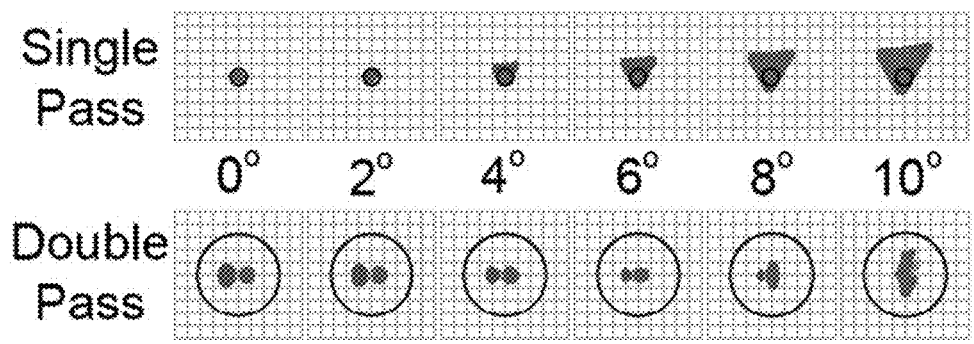

The DPSL illustrated in FIGS. 3A-B is shown in more detail with regard to FIGS. 4A-C. The DPSL enables dual-axis telecentric scanning using a single-lens configuration. FIG. 4A illustrates a first side view (specifically, from a perspective in the −x direction) of the DPSL, and FIG. 4B illustrates a second side view (specifically, from a perspective in the +y direction) of the DPSL. In addition to the d-shaped pickoff mirror 331, the double-pass optics 313, and the galvanometers 341-342, FIGS. 4A-B illustrate exemplary light paths in the DPSL. As can be seen from FIG. 4B, light passes through the double-pass optics 313 twice with each pass occurring at a different region of the double-pass optics 313.

FIGS. 3A-B and 4A-B utilize the notation $G_x$ and $G_y$ to indicate that the first and second galvanometers scan the x and y axes, respectively; however, the present disclosure is not so limited. In general, the first and second galvanometers scan orthogonal axes, but the centers of their respective mirror faces and the axis of propagation (i.e., the optical axis) of the input and output beams are co-planar. In other words, the input and the output of the DPSL are located on the same side of the DPSL.

FIG. 4C illustrates simulated spots along the beamline in the DPSL over a 10° field-of-view ("FOV") in 2° increments. The upper row in FIG. 4C illustrates the simulated spots at the mirror plane (i.e., the plane of the d-shaped pickoff mirror 331). The simulated spots at the mirror plane exhibit significant single-pass aberrations dominated by coma. The lower row in FIG. 4C illustrates the simulated spots at the output plane (i.e., the plane of the second galvanometer 342). The double-pass optics 313 corrects the aberrations on a second pass therethrough, resulting in diffraction-limited performance across the entire FOV. The double-pass spot sizes were simulated using a paraxial imaging lens with a focal length of 30 mm and an Airy radius of 12.91 μm to avoid confounding aberrations not inherent to the DPSL and allow for a direct comparison between single- and double-pass performances.

An exemplary imaging system including the SECTR engine 200 illustrated in FIG. 2 and the handheld probe 300 illustrated in FIGS. 3A-B was studied to determine the effects of the DPSL. In the OCT path, light from a single-mode fiber (NA=0.14) was collimated using a 90° off-axis parabolic mirror (an example of the parabolic mirror 351) to a 4 mm diameter. The beam was then scanned using a slow-axis galvanometer (an example of the first galvanometer 341) positioned at a 4-mm offset from the optical axis and focused telecentrically onto a d-shaped pickoff mirror (an example of the d-shaped pickoff mirror 331) using the DPSL. The beam was reflected and backpropagated through the DPSL to a fast-axis galvanometer (an example of the second galvanometer 342). The galvanometers were separated by 8 mm center-to-center to accommodate the physical size of each mirror.

The SER path utilizes a DCF for coaxial single-mode illumination and multi-mode collection that was oriented at 29° with respect to the optical axis to compensate for a custom DCF termination, which will be described in more detail below. Single-mode SER illumination was collimated to 10 mm using two achromatic doublets with a combined focal length of 26.2 mm (an example of lens systems 261 and 263), and spectrally dispersed using a 1379 line/mm polarization-independent transmission grating. The dispersed beam was then focused to an 11.5 mm line using a 54 mm focal length lens (an example of lens systems 262 and 264) and combined with the OCT path across the d-shaped pickoff mirror. The SER and OCT paths propagated collinearly with a 50 μm separation through the DPSL, a shared galvanometer (particularly, the slow-axis galvanometer), a dichroic hot mirror (an example of the dichroic mirror 361), and a 2× demagnifying telescope (an example of a system combining the scan optics 314 and the ophthalmic optics 315) to a 2 mm diameter spot on the pupil. The dichroic hot mirror allows for the placement of a visible-light fixation target, where desired.

Figure 5:
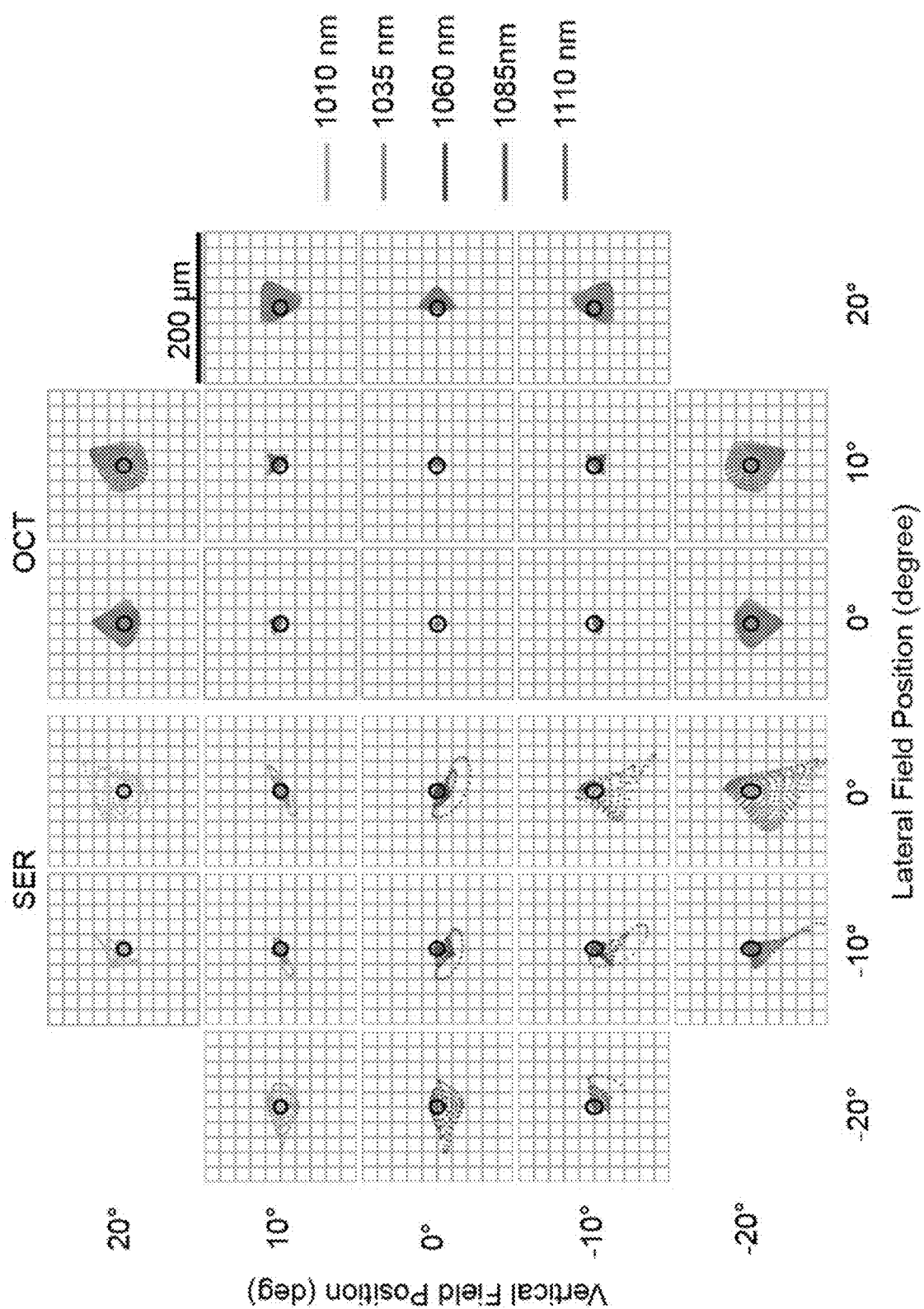
FIG. 5 illustrates exemplary simulated spot diagrams in accordance with various aspects of the present disclosure.

A modified version of the Polans eye model was used to accurately model aberrations through the human eye. FIG. 5 illustrates simulated spot diagrams for OCT and SER over a±20° FOV on the retina. The Airy radii for Oct and SER were 9.8 and 9.6 µm, respectively. Diffraction-limited OCT performance was achieved over the central 13°, and performance up to twice the diffraction limit was achieved at the FOV periphery. OCT spot sizes at the peripheral FOV were limited by the use of Ø1" optics, which were implemented to maintain a compact form factor for handheld imaging. SER spots were twice the diffraction limit on-axis and up to six times the diffraction limit at the periphery. SER imaging performance was mainly affected by single-pass propagation through the DPSL, which induced significant coma and astigmatism across the field. SER is primarily used for retinal aiming during image acquisition and motion tracking in postprocessing; thus, SECTR performance was not significantly impacted by SER lateral resolution. In any event, it is possible to precompensate for these aberrations using custom-designed collimator and objective lenses (examples of the collimating optics 311 and the focusing optics 312, respectively) where desired. Because light passes through the double-pass optics 313 twice, field curvature and lateral color aberrations were canceled.

In some aspects of the present disclosure, the DPSL may be optimized for OCT resolution as opposed to SER single-pass performance. This may result in astigmatism in the SER spots and some decrease in lateral resolution. However, the SER performance may not significantly impact SER-based registration and mosaicking methods (which will be discussed in more detail below). While a decrease in SER resolution may result in a blurring of retinal features, any blurring of retinal vessels used for registration may be treated as negligible relative to the scale of retinal motion artifacts.

Double-Clad Fiber Coupler

As noted above, single-mode illumination and multimode collection may be performed using a DCF, which may result in improved SER collection efficiency while maintaining lateral resolution. Multimode collection may also provide speckle contrast reduction through incoherent averaging of multiple spatial modes of backscattered light on the detector. When using a DCF, however, end-face reflections tend to couple into the inner cladding and may saturate backscattered SER signals from the retina. To assist with the removal of DCF end-face reflections, some aspects of the present disclosure implement an angle-polished no-core fiber ("NCF") termination. FIGS. 6A-D illustrate the effects of the angle-polished NCF termination.

Figure 6A:
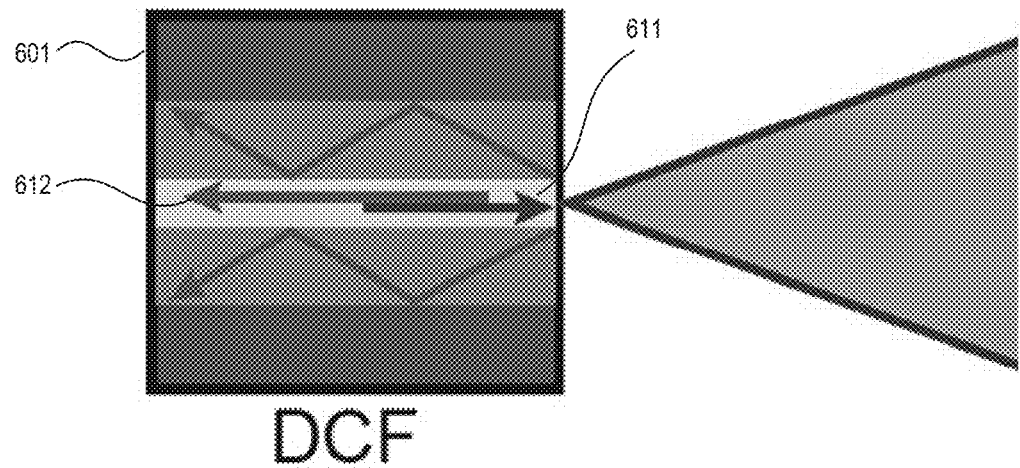
FIGS. 6A-D illustrate exemplary effects of optical systems in accordance with various aspects of the present disclosure.
Figure 6B:
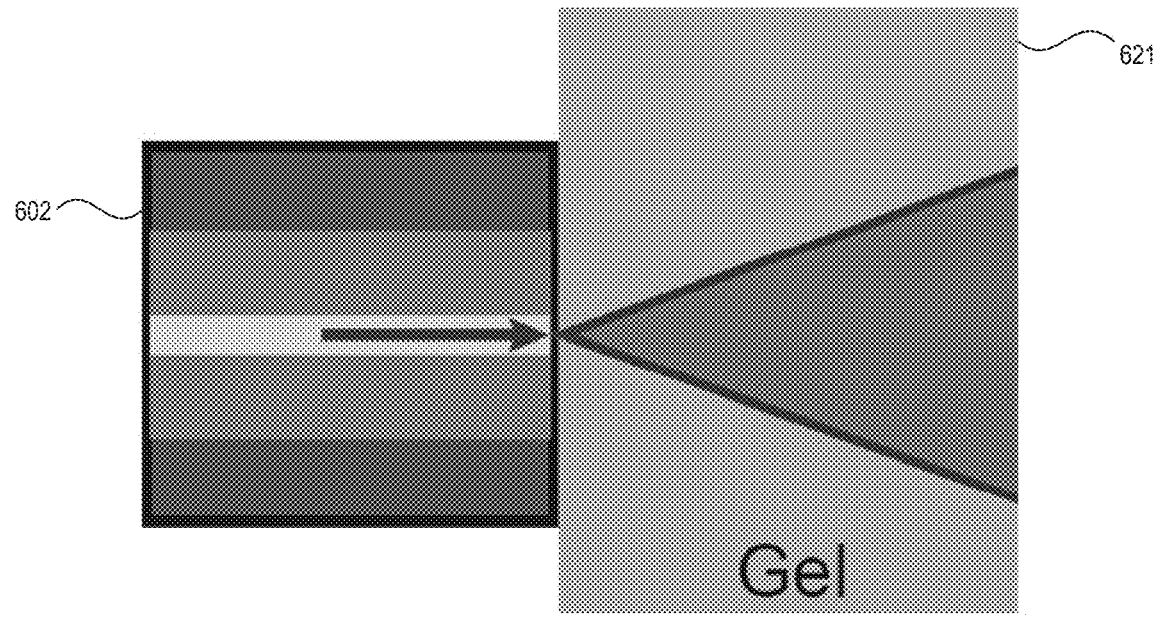

FIG. 6A illustrates a comparative example of a flat-polished DCF 601. Illumination light 611 passes through the DCF 601 and is partially reflected at the end-face thereof, resulting in backreflection light 612. FIG. 6B illustrates another comparative example of a flat-polished DCF 602 with an index-matching gel 621 disposed at the end-face. As can be seen in FIG. 6B, backreflection is eliminated reduced.

Figure 6C:
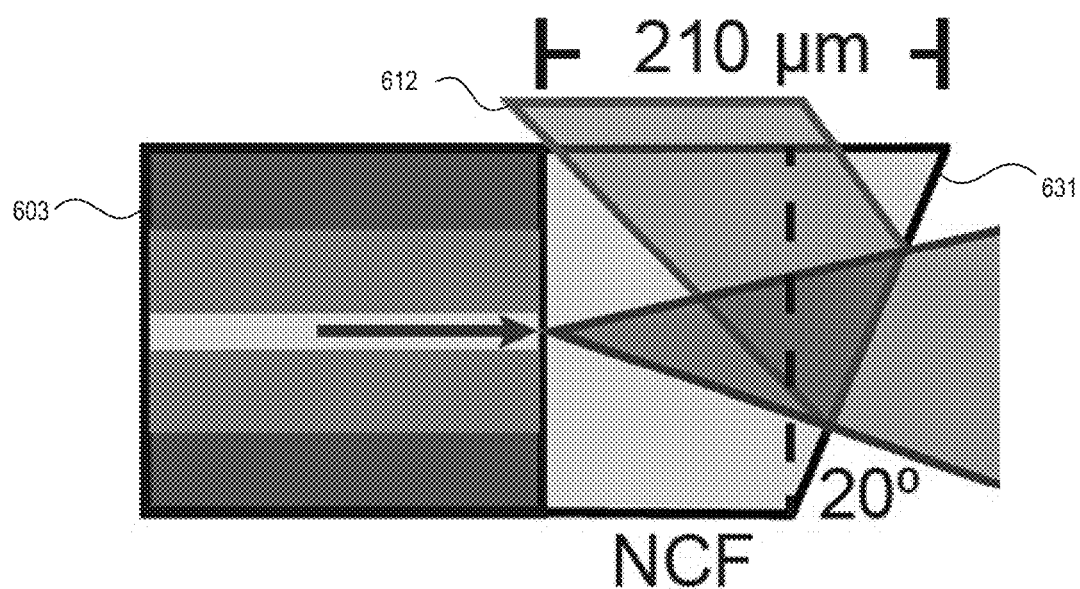

In FIG. 6C, an flat-polished DCF 603 is provided with an angle-polished NCF termination 631. As shown in FIG. 6C, backreflection does occur but the backreflection light 612 is steered out of the acceptance path of the DCF 603. In order to ensure that the backreflection light 612 is appropriately steered and that no beam clipping occurs at the output of the NCF termination 631, the output beam diameter and/or the fiber polish angles are preferably controlled. Preferably, the maximum beam diameter (which corresponds to the physical diameter of the NCF termination 631) is 125 µm, which corresponds to a maximum fiber length of 0.35 mm. As illustrated in FIG. 6C, the length of the NCF termination 631 is preferably approximately 210 µm. At such a length, the fiber polish angle is preferably approximately 20° to terminate the DCF 603, where the DCF has a single-mode core NA of 0.19, an inner cladding NA of 0.26, and an inner cladding diameter of 125 µm. The above values are exemplary and not limiting. In some aspects of the present disclosure, the beam diameter is less than 125 µm and/or the fiber polish angle is between approximately 15° and 30° (inclusive).

Figure 6D:
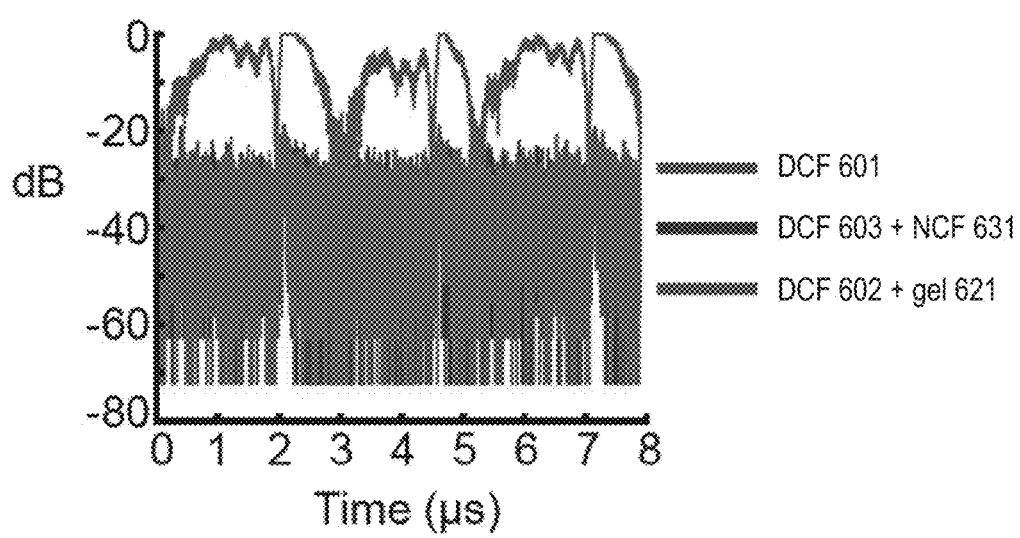

The backreflection performance of the DCFs 601-603 were compared, and FIG. 6D illustrates the results of the comparison. Specifically, FIG. 6D illustrates the results of measurements performed with no downstream optics to decouple end-face from other system reflections. The intensity of the backreflected light incident on the SER photodetector was recorded over several sweeps of the laser for each DCF configuration. As shown in FIG. 6D, a 25a-dB average backreflection reduction (relative to the DCF 601) was measured using the DCF 603 with the NCF termination 631, which is comparable to the DCF 602 including the index-matching gel 621.

Imaging and Image Processing

Where motion artifacts are present, they may be corrected by an algorithm. This algorithm may be applied in real-time (e.g., in image processing between acquisition and a live display) or in post-processing. The algorithm may further implement a mosaicking component to mosaic OCTA volumes.

In one example of the algorithm, lateral (i.e., horizontal and vertical) shifts may be computed from serial SER images and axial shifts may be computed from OCT B-scans using discrete Fourier transform registration. The measured lateral and axial shifts may then be applied to each corresponding B-scan, and OCTA may be performed using singular value decomposition on each motion-corrected volume. SER shifts may be scaled to corresponding OCT dimensions by first calculating the ration between the SER and OCT FOVs and then empirically minimizing the vessel discontinuities. The scaling ratio is constant for a given set of scan parameters; thus, manual scaling may only be performed once for each set of structural and vascular data acquired. OCTA projections may then be roughly aligned manually using overlapping fiducials; however, in some implementations the initial rough alignment may be performed automatically by the algorithm. A Frangi filter may then be applied to each OCTA projection to highlight vascular features. So-called vesselness feature maps may then be automatically aligned using an intensity-based deformable registration method and the resulting transformations may then be applied to the original OCTA volumes. Finally, the aligned OCTA volumes may be blended together to obtain a final mosaic of the overlapping datasets.

Lateral motion estimation is affected by the contrast and the number of retinal fiducials present in SER frames (e.g., blood vessels or optic nerve head). As the human peripheral retina and fovea tends to lack fiducials, this may limit the efficacy of multivolumetric registration and mosaicking in these regions. These affects are further exacerbated in OCTA, which requires small densely-sampled volumes to achieve high vascular resolution. SECTR as described herein may facilitate mosaicking because widefield SER images may be acquired concurrently with small densely-sampled OCTA volumes to ensure that motion-tracking fiducials are consistently visible. In one example, this may be achieved using a predetermined scan waveform to drive the shared SER and OCT fast-axis galvanometer such that the scan velocity is comparatively slow within the region-of-interest ("ROI"), thereby to ensure sufficiently OCTA sampling density both inside and outside the ROI. The predetermined scan waveform may allow for acquisition of widefield SER frames for motion tracking and a critically-sampled OCT volume for angiography at a fraction of the total acquisition time of a comparative example across the same FOV. In post-processing, the SER and OCT data may be resampled to linearize the line spacing and to correct the image distortions resulting from the scan waveform. Furthermore, low-pass filtering of the scan waveform may be performed by the galvanometer controller to smooth transitions between the fast and slow scan velocity regions in the resampling function.

The above processing and mosaicking algorithms may be implemented via hardware components, software modules, firmware, or combinations thereof. In some aspects of the present disclosure, the algorithms are stored in a memory associated with the SECTR engine 200 and implemented by a processor associated with the SECTR engine 200. The processor may be or implement a central processing unit ("CPU"), a field-programmable gate array ("FPGA"), an application-specific integrated circuit ("ASIC"), and the like. In some configurations, the algorithm and associated processing may be distributed among several processors. Moreover, the processors and memory need not be physically coupled to the SECTR engine 200, and instead may be remotely located (e.g., cloud-based).

Effects and Test Results

Figure 7A:
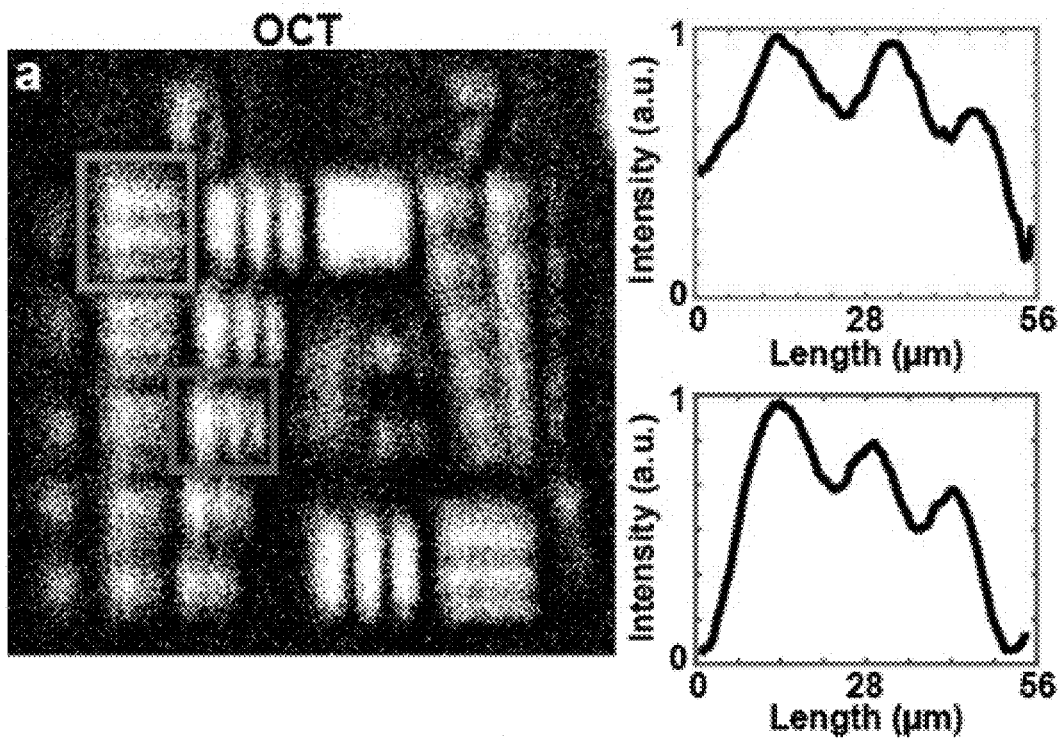
FIGS. 7A-B illustrate exemplary resolution tests performed in accordance with various aspects of the present disclosure.
Figure 7B:
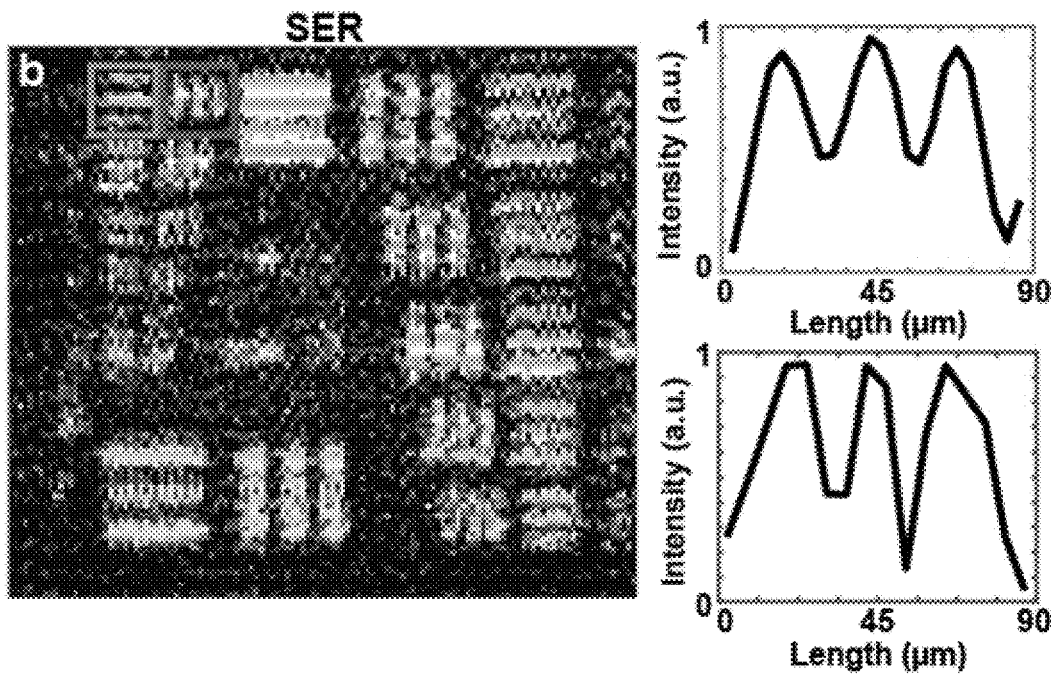

The optical performance of a handheld SECTR device utilizing a SECTR engine 200 as illustrated in FIG. 2 and a handheld probe 300 as illustrated in FIG. 3 was evaluated with regard to a reference resolution chart and in test subjects. FIGS. 7A-B illustrate the results of a resolution test performed using a USAF-1951 resolution chart, where imaging was performed in the intermediate image plane before the ophthalmic optics 315. In both FIGS. 7A-B, the resolution chart was sampled at 2560×2000×2000 pixels (spectral×lateral×frames) over a 1.1 $mm^2$ region. The images were oversampled to ensure that the resolution was limited by optical performance rather than by sampling artifacts.

FIG. 7A illustrates the en face projection of the USAF-1951 resolution chart (left) imaged with the OCT aspect of the handheld probe 300. The plot in the upper-right portion of FIG. 7A illustrates an intensity cross-section of group 6 element 2, and the plot in the lower-right portion of FIG. 7A illustrates an intensity cross-section of group 6 element 4. FIG. 7B illustrates the same projection (left) imaged with the SER aspect of the handheld probe 300. The plots in the upper-right and lower-right of FIG. 7B illustrate intensity-cross sections of group 5 element 1. As can be seen in FIGS. 7A-B, OCT fast- and slow-axes resolved group 6 elements 4 and 2 (90.5 and 71.8 lp/mm), respectively, and SER resolved group 5 element 1 (32 lp/mm).

FIGS. 8A-E illustrate the results of a resolution test performed on a healthy volunteer imaged while supine, thereby to simulate clinical imaging with an untrained photographer. The SER and OCT power incident on the pupil of the volunteer were 3.6 mW (extended line illumination) and 1.2 mW (point illumination), respectively. Widefield images were sampled at 2560×1500×1500 pixels (spectral×lines×frames) per volume in 6.125 s. As with FIGS. 7A-B, datasets were oversampled to demonstrate probe stability and motion-correction postprocessing methods over an extended acquisition time.

Figure 8A:
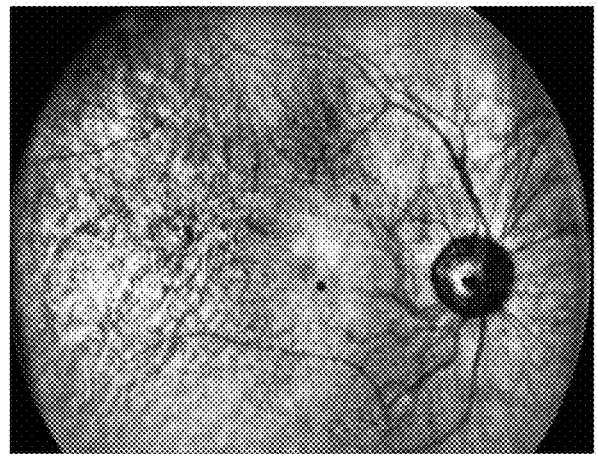
FIGS. 8A-E illustrate exemplary resolution tests performed in accordance with various aspects of the present disclosure.
Figure 8B:
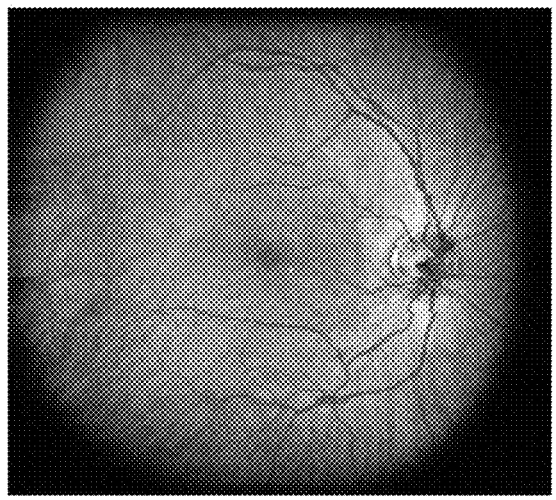
Figure 8C:
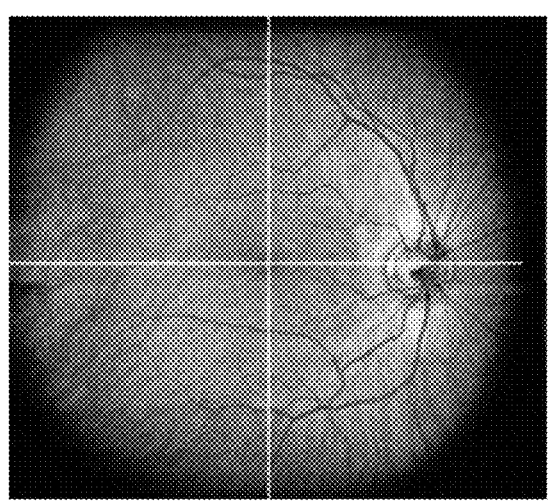
Figure 8D:
Figure 8E:
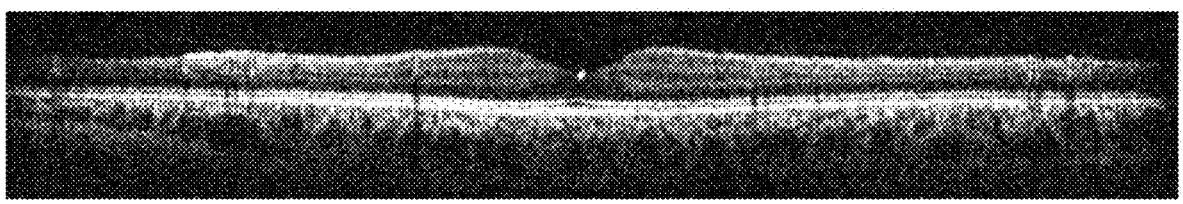

FIG. 8A illustrates a four-frame average SER frame. FIGS. 8B-C illustrate average intensity en face projections of raw and motion-corrected OCT volumes, respectively. FIG. 8C further illustrates the fast and slow axes as vertical and horizontal lines. FIGS. 8D-E illustrate representative fast-axis (FIG. 8D) and slow-axis (FIG. 8E) cross-sections from the motion-corrected volume (i.e., from FIG. 8C).

Figure 9A:
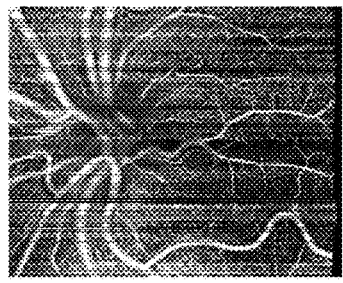
FIGS. 9A-D illustrate an exemplary mosaicking process in accordance with various aspects of the present disclosure.
Figure 9B:
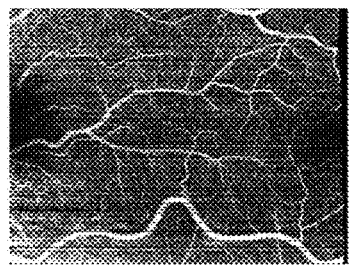
Figure 9C:
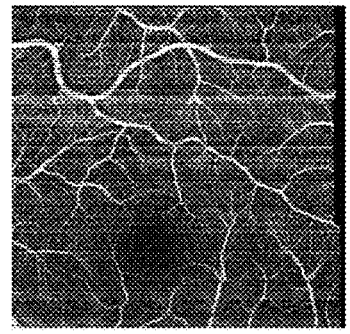
Figure 9D:
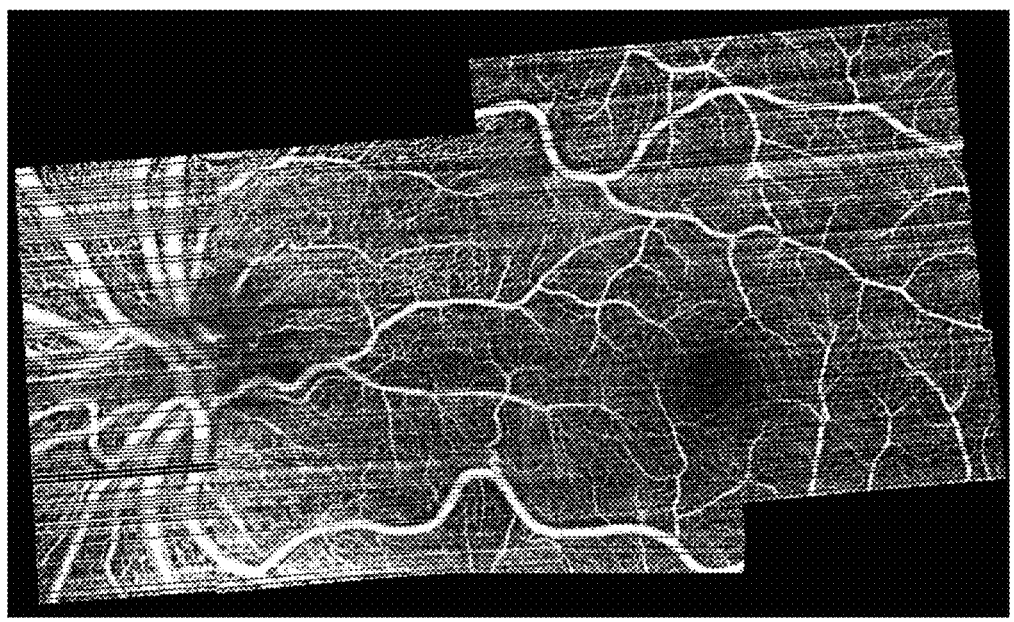

To illustrate the widefield multivolumetric mosaicking described above, handheld SECTR OCTA was performed on a second healthy volunteer in a supine position with a second untrained photographer. Three volumes were sampled at 2560×500×400 pixels (spectral×lines×frames) per volume in 3.2 s. FIGS. 9A-C illustrate these volumes after motion correction was performed. Comparing FIGS. 9A-C with one another, it can be seen that variations exist even though the volumes were acquired over the same FOV and sampling density. The variations in volume height exist due to compression and/or stretching of the data following motion correction. This effect results from motion in the OCT slow-axis and may be readily seen in FIG. 9A, where vertical motion resulted in missing data (black horizontal lines). Edges of the individual volumes were cropped prior to mosaicking to remove distorted regions resulting from nonlinear scan trajectories during galvanometer flyback. Thereafter, mosaicking was performed using the methods described above, which resulted in the image illustrated in FIG. 9D.

As such, the foregoing figures demonstrate an efficient motion-correction method in single OCT volumes and multivolumetric mosaicking of OCTA projections. Pupil vignetting can be identified on real-time SER previews to allow the system to be recentered onto the pupil, which may improve the quality of the resulting OCT/OCTA dataset. Motion correction and mosaicking also may obviate the need for repeat volume acquisitions, which reduces total imaging time and would thus improve applicability of the present disclosure to patients (e.g., pediatric patients).

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An optical relay, comprising:
    a first scan mirror configured to receive an input optical beam, and to reflect the input optical beam as a first intermediate optical beam;
    a telecentric mirror configured to receive the first intermediate optical beam, and to reflect the first intermediate optical beam as a second intermediate optical beam;
    a second scan mirror configured to receive the second intermediate optical beam, and to reflect the second intermediate optical beam as an output optical beam; and
    a lens system disposed between the telecentric mirror and the first and second scan mirrors, such that the first intermediate optical beam and the second intermediate optical beam pass through the lens system,
    wherein the telecentric mirror is separated from the lens system by a distance equal to a focal length of the lens system in a direction parallel to an optical axis of the first intermediate optical beam.

2. The optical relay according to claim 1, wherein the first scan mirror and the second scan mirror are separated from the lens system by a distance equal to a focal length of the lens system in a direction parallel to an optical axis of the second intermediate optical beam.

3. The optical relay according to claim 1, wherein an optical axis of the first intermediate optical beam and an optical axis of the second intermediate optical beam are coplanar.

4. The optical relay according to claim 1, wherein the first scan mirror is configured to scan a first axis and the second scan mirror is configured to scan a second axis orthogonal to the first axis.

5. The optical relay according to claim 1, wherein the lens system is disposed such that the first intermediate optical beam passes through a first portion of the lens system and the second intermediate optical beam passes through a second portion of the lens system.

6. The optical relay according to claim 1, wherein the lens system comprises a plurality of lenses.

7. An optical system, comprising:
    an optical engine, including:
        a light source configured to emit a source light, and
        at least one optical fiber configured to transmit the source light to an output of the optical engine; and
    a probe including an optical relay, the optical relay including:
        a first scan mirror configured to receive an input optical beam via the at least one optical fiber, and to reflect the input optical beam as a first intermediate optical beam,
        a telecentric mirror configured to receive the first intermediate optical beam, and to reflect the first intermediate optical beam as a second intermediate optical beam,
        a second scan mirror configured to receive the second intermediate optical beam, and to reflect the second intermediate optical beam as an output optical beam, and
        a lens system disposed between the telecentric mirror and the first and second scan mirrors, such that the first intermediate optical beam and the second intermediate optical beam pass through the lens system,
        wherein the telecentric mirror is separated from the lens system by a distance equal to a focal length of the lens system in a direction parallel to an optical axis of the first intermediate optical beam.

8. The optical system according to claim 7, wherein the first scan mirror and the second scan mirror are separated from the lens system by a distance equal to a focal length of the lens system in a direction parallel to an optical axis of the second intermediate optical beam.

9. The optical system according to claim 7, wherein an optical axis of the first intermediate optical beam and an optical axis of the second intermediate optical beam are coplanar.

10. The optical system according to claim 7, wherein the first scan mirror is configured to scan a first axis and the second scan mirror is configured to scan a second axis orthogonal to the first axis.

11. The optical relay according to claim 7, wherein the lens system is disposed such that the first intermediate optical beam passes through a first portion of the lens system and the second intermediate optical beam passes through a second portion of the lens system.

12. The optical system according to claim 7, wherein the lens system comprises a plurality of lenses.

13. The optical system according to claim 7, wherein the at least one optical fiber includes a first optical fiber configured to output a first portion of the source light for a first imaging operation.

14. The optical system according to claim 13, wherein the at least one optical fiber includes a second optical fiber configured to output a second portion of the source light for a second imaging operation.

15. The optical system according to claim 14, wherein the optical probe is configured to simultaneously sample a signal from the first optical fiber and from the second optical fiber.

16. The optical system according to claim 14, wherein the optical probe is configured to receive the first portion of the source light as the input optical beam.

17. The optical system according to claim 7, wherein the light source is a laser light source.

18. An optical relay, comprising:
    a first scan mirror configured to receive an input optical beam, and to reflect the input optical beam as a first intermediate optical beam;
    a telecentric mirror configured to receive the first intermediate optical beam, and to reflect the first intermediate optical beam as a second intermediate optical beam;

a second scan mirror configured to receive the second intermediate optical beam, and to reflect the second intermediate optical beam as an output optical beam; and a lens system disposed between the telecentric mirror and the first and second scan mirrors, such that the first intermediate optical beam and the second intermediate optical beam pass through the lens system, wherein the first scan mirror and the second scan mirror are separated from the lens system by a distance equal to a focal length of the lens system in a direction parallel to an optical axis of the second intermediate optical beam.

19. The optical relay according to claim 18, wherein an optical axis of the first intermediate optical beam and an optical axis of the second intermediate optical beam are coplanar.

20. An optical system, comprising:

an optical engine, including:
 a light source configured to emit a source light, and
 at least one optical fiber configured to transmit the source light to an output of the optical engine; and a probe including an optical relay, the optical relay including:

a first scan mirror configured to receive an input optical beam via the at least one optical fiber, and to reflect the input optical beam as a first intermediate optical beam, a telecentric mirror configured to receive the first intermediate optical beam, and to reflect the first intermediate optical beam as a second intermediate optical beam, a second scan mirror configured to receive the second intermediate optical beam, and to reflect the second intermediate optical beam as an output optical beam, and a lens system disposed between the telecentric mirror and the first and second scan mirrors, such that the first intermediate optical beam and the second intermediate optical beam pass through the lens system, wherein the first scan mirror and the second scan mirror are separated from the lens system by a distance equal to a focal length of the lens system in a direction parallel to an optical axis of the second intermediate optical beam.

* * * * *